United States Patent
Kimura et al.

(10) Patent No.: US 9,051,600 B2
(45) Date of Patent: Jun. 9, 2015

(54) SPHINGOMYELIN MEASUREMENT METHOD USING SEQUENTIAL PHOSPHOLIPASE D REACTIONS

(75) Inventors: Takehide Kimura, Tokyo (JP); Kazuhito Miyauchi, Tokyo (JP); Hideyuki Kuwata, Shizuoka (JP)

(73) Assignee: KYOWA MEDEX CO., LTD., Tokyo (JP)

( * ) Notice: Subject to any disclaimer, the term of this patent is extended or adjusted under 35 U.S.C. 154(b) by 0 days.

(21) Appl. No.: 14/232,427

(22) PCT Filed: Jul. 25, 2012

(86) PCT No.: PCT/JP2012/068807
§ 371 (c)(1),
(2), (4) Date: Jan. 13, 2014

(87) PCT Pub. No.: WO2013/018609
PCT Pub. Date: Feb. 7, 2013

(65) Prior Publication Data
US 2014/0162300 A1   Jun. 12, 2014

(30) Foreign Application Priority Data
Jul. 29, 2011   (JP) .................................. 2011-166458

(51) Int. Cl.
  C12Q 1/44    (2006.01)
  C12Q 1/61    (2006.01)
  G01N 33/92   (2006.01)
  C12Q 1/28    (2006.01)

(52) U.S. Cl.
  CPC *C12Q 1/61* (2013.01); *G01N 33/92* (2013.01); *C12Q 1/28* (2013.01); *C12Q 1/44* (2013.01); *C12Y 101/03017* (2013.01); *C12Y 301/01005* (2013.01); *C12Y 301/04004* (2013.01)

(58) Field of Classification Search
USPC .......................................................... 435/19
See application file for complete search history.

(56) References Cited

U.S. PATENT DOCUMENTS

2009/0148877 A1* 6/2009 Jiang et al. ..................... 435/21
2010/0255516 A1* 10/2010 Itoh et al. ...................... 435/11

FOREIGN PATENT DOCUMENTS

| JP | 06-197793 | 7/1994 |
| JP | 06-197794 | 7/1994 |
| JP | 09-023897 | 1/1997 |
| JP | 2009-519713 | 5/2009 |
| WO | 01/80903 | 11/2001 |
| WO | 2007/078806 | 7/2007 |
| WO | 2009/048143 | 4/2009 |

OTHER PUBLICATIONS

Nakamura S. et al. Mammalian Phospholipase D. Proc Natl Acad Sci USA 93:4300-4, Apr. 1996.*
Hojjati M. et al. Rapid, Specific, and Sensitive Measurements of Plasma Sphingomyelin and Phosphatidylcholine. J of Lipid Research 47(3)673-676, Mar. 2006.*
He, X. et al. A Fluorescence Based High Throughput Sphingomyelin Assay . . . Analytical Biochemistry 306(1)115-123, Jul. 1, 2002.*
Fujii, et al., "Chromogenic Assay for the Activity of Sphingomyelinase from *Bacillus cereus* and Its Application to the Enzymatic Hydrolysis of Lysophospholipids", Biol. Pharm. Bull. vol. 27, No. 11 (2004) 1725-29.
Imamura, et al., "Purification of *Streptomyces chromofuscus* Phospholipase D by Hydrophobic Affinity Chromatography on Palmitoyl Cellulose", J. Biochem., vol. 85, No. 1 (1979) 79-95.
Jiang, et al., "Plasma Sphingomyelin Level as a Risk Factor for Coronary Artery Disease", Arterioscler Thromb Vasc. Biol., vol. 20 (2000) 2614-18.
Nelson, et al., "Plasma Sphingomyelin and Subclinical Atherosclerosis: Findings from the Multi-Ethnic Study of Atherosclerosis", Am. J. Epidemiol., vol. 163, No. 10 (2006) 903-12.
Park, et al., "Inhibition of Sphingomyelin Synthesis Reduces Atherogenesis in Apolipoprotein E-Knockout Mice", Circulation, vol. 110, No. 22 (2004) 3465-71.
Rombaut, et al., "Analysis of Phospho- and Sphingolipids in Dairy Products by a New HPLC Method", J. Dairy Sci., vol. 88, No. 2 (2005) 482-88.
Schlitt, et al., "Further evaluation of plasma sphingomyelin levels as a risk factor for coronary artery disease", Nutrition & Metabolism, vol. 3 (2006) 1-8.
Kyowa Medex Co., Ltd., Rin Shishitsu Kit Jido Bunseki Sochi-yo (Phospholipid Kit Determiner L PL Catalog) (2008), English translation.

* cited by examiner

*Primary Examiner* — Ralph Gitomer
(74) *Attorney, Agent, or Firm* — Fitzpatrick, Cella, Harper & Scinto (57) ABSTRACT

Provided is a method for simply and accurately measuring sphingomyelin in a sample, and a kit therefore. The method is a method for measuring sphingomyelin in a sample, comprising reacting the sample with a phospholipase D which does not react with sphingomyelin and lysophosphatidylcholine but reacts with phosphatidylcholine, a lysophospholipase or a monoglyceride lipase, and a choline oxidase, eliminating the formed hydrogen peroxide, reacting the resultant with a phospholipase D which does not react with glycerol-3-phosphorylcholine and free fatty acid but reacts with sphingomyelin, and a choline oxidase, and measuring the formed hydrogen peroxide.

30 Claims, 3 Drawing Sheets

SPHINGOMYELIN MEASUREMENT METHOD USING SEQUENTIAL PHOSPHOLIPASE D REACTIONS

This application is a National Phase of PCT/JP2012/068807 filed Jul. 25, 2012, which in turn claims benefit of Japanese Application No. 2011-166458 filed Jul. 29 2011.

TECHNICAL FIELD

The present invention relates to a method and a kit for measuring sphingomyelin.

BACKGROUND ART

The blood comprises lipoproteins such as high density lipoprotein (hereinafter abbreviated as HDL), low density lipoprotein (hereinafter abbreviated as LDL), very low density lipoprotein (hereinafter abbreviated as VLDL), and chylomicron (hereinafter abbreviated as CM). These lipoproteins are different in the percentage of components such as cholesterol, triglyceride, phospholipid, and protein, and have different functions in vivo. A lipoprotein mainly comprises 3 types of phospholipids, i.e., phosphatidylcholine (hereinafter abbreviated as PC), lysophosphatidylcholine (hereinafter abbreviated as LPC), and sphingomyelin, thereinafter abbreviated as SM).

PC and SM are major phospholipids among these 3 types of phospholipids and account for approximately 70% and 20% of the total phospholipids, respectively. SM is known to accumulate in atheroma in human and animal models. LDL present in human arteriosclerotic lesions comprises a large amount of SM compared to LDL in the plasma (Non-patent Document 1).

Clinical researches in humans also showed that both of plasma SM and SM/PC ratio are independent risk factors for ischemic heart disease (Non-patent Document 2 to 4).

Hitherto, a method using thin-layer chromatography and a method using high-performance liquid chromatography were reported as a method for measuring SM (Non-patent Document 5); however, they have drawbacks such as being cumbersome in operation and requiring a long time for measurement. An enzymatic measurement method utilizing bacterial sphingomyelinase was also reported (Patent Document 1 and Non-patent Document 2). This measurement method is a method for measuring sphingomyelin by hydrolyzing sphingomyelin to phosphorylcholine and n-acylsphingosine by bacterial sphingomyelinase, hydrolyzing the formed phosphorylcholine to choline by alkaline phosphatase, reacting the formed choline with choline oxidase, and measuring the formed hydrogen peroxide. However, the measurement method has problems, such as influence of the use of alkaline phosphatase on the measurement of other components to be measured and specificity of sphingomyelinase of reacting with LPC as well as SM (Non-patent Document 6).

PRIOR ART DOCUMENTS

Patent Documents

Patent Document 1: Japanese unexamined Patent application Publication (Translation of PCT Application) No. 2009-519713

Non-Patent Documents

Non-patent Document 1: Circulation, Vol. 110 (22), p. 3465-3471 (2004)

Non-patent Document 2: Arterioscler Thromb Vasc Biol., Vol. 20, p. 2614-2618 (2000)

Non-patent Document 3: Nutrition & Metabolism, Vol. 3, p. 5 (2006)

Non-patent Document 4: Am. J. Epidemiol., Vol. 163, p. 903-912 (2006)

Non-patent Document 5: Dairy Sci., Vol. 88, p. 482-488 (2005)

Non-patent Document 6: Biol. Pharm. Bull. Vol. 27, p. 1725-1729 (2004)

SUMMARY OF THE INVENTION

Problems to be Solved by the Invention

An object of the present invention is to provide a method and a kit for simply and accurately measuring SM in a sample.

Means to Solve the Object

The present inventors hare conducted intensive studies for solving the above problems, and have found that in a method for selectively measuring SM in a sample comprising PC, LPC, and SM, SM can be specifically measured by using a phospholipase D which does not react with glycerol-3-phosphorylcholine and free fatty acid formed by the reaction of LPC with a lysophospholipase or a monoglyceride lipase but reacts with SM, thereby accomplishing the present invention. Specifically, the present invention relates to [1] to [17] below.

[1] A method for measuring SM in a sample, comprising reacting the sample with a phospholipase D which does not react with SM and LPC but reacts with PC, a lysophospholipase or a monoglyceride lipase, and a choline oxidase, eliminating the formed hydrogen peroxide, reacting the resultant with a phospholipase D which does not react with glycerol-3-phosphorylcholine and free fatty acid but reacts with SM, and a choline oxidase, and measuring the formed hydrogen peroxide.

[2] A method for measuring SM in a sample, comprising reacting the sample with a phospholipase D which does not react with SM and LPC but reacts with PC, a lysophospholipase or a monoglyceride lipase, an oxidized coenzyme, a choline dehydrogenase, and a reduced coenzyme oxidase, eliminating the formed hydrogen peroxide, reacting the resultant with a phospholipase D which does not react with glycerol-3-phosphorylcholine and free fatty acid but reacts with SM, an oxidized coenzyme, a choline dehydrogenase, and a reduced coenzyme oxidase, and measuring the formed hydrogen peroxide.

[3] The method according to [1], wherein the reaction of the sample with the phospholipase D which does not react with SM and LPC but reacts with PC, the lysophospholipase or the monoglyceride lipase, and the choline oxidase is performed in the presence of a catalase, and the reaction of the resultant with the phospholipase D which does not react with glycerol-3-phosphorylcholine and free fatty acid but reacts with SM, and the choline oxidase is performed in the presence of a catalase inhibitor.

[4] The method according to [2], wherein the reaction of the sample with the phospholipase D which does not react with SM and LPC but reacts with PC, the lysophospholipase or the monoglyceride lipase, the oxidized coenzyme, the choline dehydrogenase, and the reduced coenzyme oxidase is performed in the presence of a catalase, and the reaction of the resultant with the phospholipase D which does not react with glycerol-3-phosphorylcholine and free fatty acid but reacts with SM, the oxidized coenzyme, the choline dehydrogenase, and the reduced coenzyme oxidase is performed in the presence of a catalase inhibitor.

[5] The method according to [3] or [4], wherein the catalase inhibitor is an azide.

[6] The method according to [1] or [2], wherein the eliminating of hydrogen peroxide is performed in the presence of a peroxidase and one of a pair of oxidative coupling-coloring chromogens, and the measurement of hydrogen peroxide is performed in the presence of a peroxidase and the pair of oxidative coupling-coloring chromogens.

[7] The method according to any one of [1] to [5], wherein the measurement of hydrogen peroxide is performed in the presence of a peroxidase and a leuco chromogen.

[8] The method according to any one of [1] to [7], wherein the phospholipase D which does not react with SM and LPC but reacts with PC is a phospholipase D derived from *Streptomyces* sp.

[9] The method according to any one of [1] to [8], wherein the phospholipase D which does not react with glycerol-3-phosphorylcholine and free fatty acid but reacts with SM is a phospholipase D derived from *Streptomyces chromofuscus*.

[10] A kit for measuring SM in a sample, comprising a first reagent comprising a phospholipase D which does not react with SM and LPC but reacts with PC, a lysophospholipase or a monoglyceride lipase, a choline oxidase, and a catalase, and a second reagent comprising a phospholipase D which does not react with glycerol-3-phosphorylcholine and free fatty acid but reacts with SM and a catalase inhibitor.

[11] A kit for measuring SM in a sample, comprising a first reagent comprising a phospholipase D which does not react with SM and LPC but reacts with PC, a lysophospholipase or a monoglyceride lipase, a choline oxidase, a peroxidase, and one of a pair of oxidative coupling-coloring chromogens, and a second reagent comprising a phospholipase D which does not react with glycerol-3-phosphorylcholine and free fatty acid but reacts with SM and the other of the pair of oxidative coupling-coloring chromogens.

[12] A kit for measuring SM in a sample, comprising a first reagent comprising a phospholipase D which does not react with SM and LPC but reacts with PC, a lysophospholipase or a monoglyceride lipase, a choline dehydrogenase, an oxidized coenzyme, a reduced coenzyme oxidase, and a catalase, and a second reagent comprising a phospholipase D which does not react with glycerol-3-phosphorylcholine and free fatty acid but reacts with SM, and a catalase inhibitor.

[13] A kit for measuring SM in a sample, comprising a first reagent comprising a phospholipase D which does not react with SM and LPC but reacts with PC, a lysophospholipase or a monoglyceride lipase, a choline dehydrogenase, an oxidized coenzyme, a reduced coenzyme oxidase, a peroxidase, and one of a pair of oxidative coupling-coloring chromogens, and a second reagent comprising a phospholipase D which does not react with glycerol-3-phosphorylcholine and free fatty acid but reacts with SM and the other of the pair of oxidative coupling-coloring chromogens.

[14] The kit according to [10] or [12], wherein the catalase inhibitor is an azide.

[15] The kit according to [10], [12], or [14], wherein each of a peroxidase and the leuco chromogen is comprised in a different reagent of the first reagent and the second reagent, respectively.

[16] The kit according to any one of [10] to [15], wherein the phospholipase D which does not react with SM and LPC but reacts with PC is a phospholipase D derived from *Streptomyces* sp.

[17] The kit according to any one of [10] to [16], wherein the phospholipase D which does not react with glycerol-3-phosphorylcholine and free fatty acid but reacts with SM is a phospholipase D derived from *Streptomyces chromofuscus*.

Effect of the Invention

According to the present invention, a method and a kit for simply and accurately measuring SM in a sample are provided.

MODE FOR CARRYING OUT THE INVENTION

<Method for Measuring SM>

The method for measuring SM according to the present invention is a method which does not require the operation of separating SM.

The method tor measuring SM according to the present invention is a method for measuring SM in a sample, comprising reacting the sample with a phospholipase D which does not react with SM and LPC but reacts with PC, a lysophospholipase or a monoglyceride lipase, and a choline oxidase, eliminating the formed hydrogen peroxide, reacting the resultant with a phospholipase D which does not react with glycerol-3-phosphorylcholine and free fatty acid but reacts with SM, and a choline oxidase, and measuring the formed, hydrogen peroxide. Specific examples thereof include a method comprising the steps of:

(1) reacting a sample with a phospholipase D which does not react with SM and LPC but reacts with PC, a lysophospholipase or a monoglyceride lipase, and a choline oxidase to form hydrogen peroxide glycerol-3-phosphorylcholine, and free fatty acid;

(2) eliminating hydrogen peroxide formed in step (1);

(3) reacting SM in the reaction solution after step (2) with a phospholipase D which does not react with glycerol-3-phosphorylcholine and free fatty acid but reacts with SM, and the choline oxidase to form hydrogen peroxide; and (4) measuring the hydrogen peroxide formed in step (3).

The concentration of SM in a sample can be determined as follows. First, measurement by the above steps is performed using a standard with a known SM concentration as the sample in step (1) to prepare a calibration curve showing the relationship between SM concentrations and measured values. Then, measurement by the above steps is performed using an actual sample, and the obtained measured value is correlated with the calibration curve prepared above to determine the SM concentration in the sample.

The choline oxidase used in step (3) may be the choline oxidase used in step (1) or the choline oxidase newly added.

Table 1 shows a principle diagram of the method for measuring SM according to the present invention by the above steps.

rylcholine and free fatty acid but reacts with SM, and the choline is further converted to hydrogen peroxide by the choline oxidase. Here, glycerol-3-phosphorylcholine and free fatty acid generated in step (2) do not react with the phospholipase D which does not react with glycerol-3-phosphorylcholine and free fatty acid but reacts with SM; thus, hydrogen peroxide is formed from SM remaining in the reac-

TABLE 1

| | | | | | | | |
|---|---|---|---|---|---|---|---|
| Eliminating Reaction | { Phosphatidylcholine (PC) | $\xrightarrow{\text{PLD}^*}$ | Choline | $\xrightarrow{\text{CLOD}}$ | $H_2O_2$ | Hydrogen Peroxide Eliminating System $\longrightarrow$ | Eliminated |
| | Lysophosphatidylcholine (LPC) | $\xrightarrow{\text{MGLP or LYPL}}$ | | | Glycerol-3-phosphorylcholine + Free Fatty Acid | | |
| Main Reaction | Sphingomyelin (SM) | $\xrightarrow{\text{PLD}}$ | Choline | $\xrightarrow{\text{CLOD}}$ | $H_2O_2$ | Hydrogen Peroxide Eliminating System $\longrightarrow$ | Dye or the like |

PLD*: Phospholipase D Which Does Not Reach with SM and LPC but Reacts with PC
CLOD: Choline Oxidase
LYPL: Lysophospholipase
MGLP: Monoglyceride lipase
PLD: Phospholipase D Which Does Not React with Glycerol-3-phosphorycholine and Free Fatty Acid but Reacts with SM
Hydrogen Peroxide Eliminating System: (1) Catalase; (2) Peroxidase, One of a Pair of Oxidative Coupling-Coloring Chromogens
Hydrogen Peroxide Measurement System: (1) Electrode for Hydrogen Peroxide Detection; (2) Peroxidase, Oxidative Coupling-Coloring Chromogens, and the like Sphinhomyelin (SM)

Phosphatidylcholine (PC)

Lysophosphatidylcholine (LPC)
[X:H, Y:C(=O)R or X:C(=O)R, Y:H]

In step (1) of the above method, PC is converted to choline by the phospholipase D which does not react with SM and LPC but reacts with PC and the choline is further converted to hydrogen peroxide by the choline oxidase. LPC is also converted to glycerol-3-phosphorylcholine and free fatty acid by the lysophospholipase or the monoglyceride lipase. Hydrogen peroxide formed in step (1) is eliminated in step (2). In the measurement method according to the present invention, the eliminating of hydrogen peroxide means converting hydrogen peroxide formed from PC to a substance which does not affect the measurement of SM. The eliminating of hydrogen peroxide can be performed, for example, by reacting hydrogen peroxide formed from PC with a catalase to convert the hydrogen peroxide to water, or by reacting hydrogen peroxide formed from PC with a peroxidase and one of a pair oxidative coupling-coloring chromogens described later to convert it to a colorless substance.

Then, in step (3), SM is converted to choline by the phospholipase D which does not react with glycerol-3-phosphotion solution. The hydrogen peroxide formed from SM is measured, in step (4).

The method tor measuring SM according to the present invention is also a method for measuring SM in a sample, comprising reacting the sample with a phospholipase D which does not react with SM and LPC but reacts with PC, a lysophospholipase or a monoglyceride lipase, an oxidized coenzyme, a choline dehydrogenase, and a reduced coenzyme oxidase, eliminating the formed hydrogen peroxide, reacting the resultant with a phospholipase D which does not react with glycerol-3-phosphorylcholine and free fatty acid but reacts with SM, an oxidized coenzyme, a choline dehydrogenase, and a reduced coenzyme oxidase, and measuring the formed hydrogen peroxide. Specific examples thereof include a method comprising the steps of:

(1) reacting a sample with a phospholipase D which does not react with SM and LPC but reacts with PC, a lysophospholipase or a monoglyceride lipase, an oxidized coenzyme, a choline dehydrogenase, and a reduced coenzyme oxidase to form hydrogen peroxide, a reduced coenzyme, glycerol-3-phosphorylcholine, and free fatty acid;

(2) eliminating the hydrogen peroxide formed in step (1);

(3) reacting SM in the reaction solution after step (2) with a phospholipase D which does not react with glycerol-3-phosphorylcholine and free fatty acid but reacts with SM, the choline dehydrogenase, the oxidized coenzyme, and the reduced coenzyme oxidase used in step (1) or those newly added.

Table 2 shows a principle diagram of the method for measuring SM according to the present invention by the above steps.

TABLE 2

PLD*: Phospholipase D Which Does Not Reach with SM and LPC but Reacts with PC
CLDH: Choline Dehydrogenase
LYPL: Lysophospholipase
MGLP: Monoglyceride lipase
PLD: Phospholipase D Which Does Not React with Glycerol-3-phosphorycholine and Free Fatty Acid but Reacts with SM
Hydrogen Peroxide Eliminating System: (1) Catalase; (2) Peroxidase, One of a Pair of Oxidative Coupling-Coloring Chromogens
Hydrogen Peroxide Measurement System: (1) Hydrogen Peroxide Electrode; (2) Peroxidase, Oxidative Coupling-Coloring Chromogens, and the like Sphinhomyelin (SM)

Phosphatidylcholine (PC)

Lysophosphatidylcholine (LPC)
[X:H, Y:C(=O)R or X:C(=O)R, Y:H]

oxidized coenzyme, the choline dehydrogenase, and the reduced coenzyme oxidase to form hydrogen peroxide and the reduced coenzyme; and (4) measuring the hydrogen peroxide formed in step (3).

The concentration of SM in a sample can be determined as follow. First, measurement by the above steps is performed using a standard with a known SM concentration as the sample in step (1) to prepare a calibration curve showing the relationship between SM concentrations and measured values. Then, measurement by the above steps is performed using an actual sample, and the obtained measured value is correlated with the calibration curve prepared above to determine the SM concentration in the sample.

The choline dehydrogenase, the oxidized coenzyme, and the reduced coenzyme oxidase used in step (3) may be the In step (1) of the above method, PC is converted to choline by the phospholipase D which does not react with SM and LPC but reacts with PC and the choline is further converted to hydrogen peroxide by the choline oxidase, the oxidized coenzyme, and the reduced coenzyme oxidase. LPC is also converted to glycerol-3-phosphorylcholine and free fatty acid by the lysophospholipase or the monoglyceride lipase. Hydrogen peroxide formed in step (1) is eliminated in step (2). In the measurement method according to the present invention, the eliminating of hydrogen peroxide means converting hydrogen peroxide formed from PC to a substance which does not affect the measurement of SM. The eliminating of hydrogen peroxide can be performed, for example, by reacting hydrogen peroxide formed from PC with a catalase to convert the hydrogen peroxide to water, or by reacting hydrogen peroxide formed from PC with a peroxidase and one of a pair of oxidative coupling-coloring chromogens described later to convert it to a colorless substance.

Then, in step (3), SM is converted to choline by the phospholipase D which does not react with glycerol-3-phosphorylcholine and free fatty acid but reacts with SM, and the choline is further converted to hydrogen peroxide by the choline oxidase. Here, glycerol-3-phosphorylcholine and free fatty acid generated in step (2) do not react with the phospholipase D which does not react with glycerol-3-phosphorylcholine and free fatty acid but reacts with SM; thus, hydrogen peroxide is formed from SM remaining in the reaction solution. The hydrogen peroxide generated from SM is measured in step (4).

In the measurement method according to the present invention, steps (1) and (2) can be performed stepwise or simultaneously, and they are preferably performed simultaneously. The reaction temperature in steps (1) and (2) is generally 10 to 50° C., preferably 20 to 40° C., and the reaction time is generally 1 to 60 minutes, preferably 2 to 30 minutes.

In case the hydrogen peroxide formed in step (1) is eliminated using a catalase in step (2), the reaction in step (3) is preferably performed in the presence of a catalase inhibitor. Examples of the catalase inhibitor include an azide. Examples of the azide include lithium azide, sodium azide, and potassium azide.

In step (4), the hydrogen peroxide formed in step (3) can be measured, for example, by reacting the hydrogen peroxide with a leuco chromogen described later or the pair of oxidative coupling-coloring chromogens in the presence of a peroxidase and measuring the absorbance of the formed dye. Particularly, in case the hydrogen peroxide formed in step (1) is eliminated using a peroxidase and one of the pair of oxidative coupling-coloring chromogens, the other of the pair of oxidative coupling-coloring chromogens is preferably added in the reaction of step (3). In this case, the hydrogen peroxide formed in step (3) can be measured in step (4) by reacting the hydrogen peroxide with a pair of oxidative coupling-coloring chromogens in the presence of a peroxidase and measuring the absorbance of the formed dye.

In the measurement method according to the present invention, steps (3) and (4) can be performed stepwise or simultaneously, and they are preferably performed simultaneously. The reaction temperature in steps (3) and (4) is generally 10 to 50° C., preferably 20 to 40° C., and the reaction time is generally 1 to 60 minutes, preferably 2 to 30 minutes.

The measurement method according to the present invention can be applied to dry chemistry of point of care testing (POCT), and it is preferably performed in an aqueous medium described later.

SM can also be measured by reacting the hydrogen peroxide formed from PC with a peroxidase and an oxidative coloring chromogen described later for conversion to a dye to measure the absorbance (A1) of the reaction solution; similarly converting the hydrogen peroxide formed from SM to a dye to measure the absorbance (A2) of the reaction solution; and subtracting the absorbance (A1) from the absorbance (A2). In this method, a fluorescent substance (for example, 4-hydroxyphenylacetic acid, 3-(4-hydroxyphenyl)propionic acid, or coumarin) or a luminescent substance (for example, a luminol compound or a lucigenin compound) can also be used in place of the oxidative coloring chromogen, SM can be measured by measuring the fluorescence intensity of the reaction solution in case the fluorescent substance is used or by measuring luminescence intensity of the reaction solution in case the luminescent substance is used. SM can also be measured by measuring hydrogen peroxide formed from PC and hydrogen peroxide formed from SM using an electrode for hydrogen peroxide detection. These methods are encompassed in the measurement method according to the present invention.

In addition, in case the hydrogen peroxide in step (2) is eliminated using the catalase, the hydrogen peroxide formed in step (3) can also be measured in step (4) by reacting the hydrogen peroxide with a fluorescent substance or a luminescent substance in the presence of the catalase inhibitor and a peroxidase to measure the intensity of the generated fluorescence or luminescence. Examples of the fluorescent and luminescent substances include the aforementioned fluorescent and luminescent substances.

Examples of the sample in the present invention include whole blood, plasma, serum, spinal fluid, saliva, amniotic fluid, urea, sweat, and pancreatic juice, and plasma and serum are preferable.

The phospholipase D which does not react with SM and LPC but reacts with PC in the present invention is not particularly limited as long as it is a phospholipase D which reacts with PC but does not react with SM and LPC; examples thereof include a phospholipase D derived from an animal, a plant, or a microorganism, and a phospholipase D produced by a genetic engineering technique. Examples of the microorganism-derived phospholipase D include a phospholipase D derived from *Streptomyces* sp. The phospholipase D may also be a commercially available one. Examples of the commercially available phospholipase D include Phospholipase D (PLDP made by Asahi Kasei Corporation). In the present invention, a combination of two or more phospholipase Ds which do not react with SM and LPC but react with PC can also be used.

The lysophospholipase in the present invention is not particularly limited as long as it is a lysophospholipase having hydrolytic activities against LPC; examples thereof include a lysophospholipase derived from an animal, a plant, or a microorganism, and a lysophospholipase produced by a genetic engineering technique. The lysophospholipase may also be a commercially available one. Examples of the commercially available lysophospholipase include Lysophospholipase (LYPL made by Asahi Kasei Corporation).

The monoglyceride lipase in the present invention is not particularly limited as long as it as a monoglyceride lipase having hydrolytic activities against LPC; examples thereof include a monoglyceride lipase derived from an animal, a plant, or a microorganism, and a monoglyceride lipase produced by a genetic engineering technique. The monoglyceride lipase may also be a commercially available one. Examples of the commercially available monoglyceride lipase include Monoglyceride lipase (MGLP made by Asahi Kasei Corporation).

In the present invention, a combination of two or more lysophospholipases or monoglyceride lipases can also be used.

In the method for measuring SM of the present invention, the concentration of the phospholipase D which does not react with SM and LPC but reacts with PC in the reaction solution is not particularly limited as long as it is a concentration which enables the measurement of SM according to the present invention; it is generally 0.001 to 200,000 U/L, preferably 0.005 to 100,000 U/L.

In the method for measuring SM of the present invention, the concentration of the lysophospholipase or the monoglyceride lipase in the reaction solution is not particularly limited as long as it is a concentration which enables the measurement of SM according to the present invention; it is generally 0.001 to 200,000 U/L, preferably 0.005 to 100,000 U/L.

The choline oxidase in the present invention is not particularly limited as long as it is an enzyme having the ability to oxidize choline to form hydrogen peroxide; there can also be used, for example, a choline oxidase derived from an animal, a plant, or a microorganism as well as a choline oxidase produced by a genetic engineering technique. Commercially available products can also be used such as Choline Oxidase (CLOD made by Kyowa Hakko Co., Ltd.) and Choline Oxidase (CHO-301 made by Toyobo Co., Ltd.). In the present invention, a combination of two or more choline oxidases can also be used.

In the method for measuring SM of the present invention, the concentration of the choline oxidase in the reaction solution is not particularly limited as long as it is a concentration which enables the measurement of SM according to the present invention; it is generally 0.001 to 200,000 U/L, preferably 0.005 to 20,000 U/L.

The phospholipase D which does not react with glycerol-3-phosphorylcholine and free fatty acid but reacts with SM in the present invention is not particularly limited as long as it is a phospholipase D which does not react with glycerol-3-phosphorylcholine and free fatty acid but reacts with SM; there can also be used, for example, a phospholipase D derived from an animal, a plant, or a microorganism, a lipoprotein lipase having phospholipase D activities, as well as a phospholipase D produced by a genetic engineering technique. Examples of the phospholipase D derived from a microorganism include a phospholipase D derived from *Streptomyces chromofuscus*. The phospholipase D which does not react with glycerol-3-phosphorylcholine and free fatty acid but reacts with SM may also be a commercially available one. Examples of the commercially available phospholipase D which does not react with glycerol-3-phosphorylcholine and free fatty acid but reacts with SM include Phospholipase D (PLD made by Asahi Kasei Corporation). In the present invention, a combination of two or more phospholipase Ds which do not react with glycerol-3-phosphorylcholine and free fatty acid but react with SM can also be used.

In the method for measuring SM of the present invention, the concentration of the phospholipase D which does not react with glycerol-3-phosphorylcholine and free fatty acid but reacts with SM in the reaction solution is not particularly limited as long as it is a concentration which enables the measurement of SM according to the present invention; it is generally 0.001 to 500,000 U/L, preferably 0.005 to 250,000 U/L.

The choline dehydrogenase in the present invention is not particularly limited as long as it is an enzyme having the ability so oxidize choline in the presence of an oxidized coenzyme to form a reduced coenzyme; there can also be used, for example, a choline dehydrogenase derived from an animal, a plant, or a microorganism as well as a choline dehydrogenase produced by a genetic engineering technique. In the present invention, a combination of two or more choline dehydrogenases can also be used.

In the method for measuring SM of the present invention, the concentration of the choline dehydrogenase in the reaction solution is not particularly limited as long as it is a concentration which enables the measurement of SM according to the present invention; it is generally 0.001 to 200,000 U/L, preferably 0.005 to 100,000 U/L.

Examples of the oxidized coenzyme used in the measurement using the choline dehydrogenase include $NAD(P)^{30}$ and thio-NAD $(P)^+$. Examples of the reduced coenzyme formed by the reaction of the choline dehydrogenase include NAD(P)H and thio-NAD(P)H.

The concentration of the oxidized coenzyme used in the method for measuring SM according to the present invention in the reaction solution is not particularly limited as long as it is a concentration which enables the measurement of SM according to the present invention; it is generally 0.01 to 400 mmoles/L, preferably 0.1 to 100 mmoles/L.

The reduced coenzyme oxidase in the present invention is not particularly limited as long as it is an enzyme having the ability to form hydrogen peroxide from the reduced coenzyme formed by the reaction of the choline dehydrogenase; examples thereof include NAD (P)H oxidase. The reduced coenzyme oxidase may also be a commercially available one. Examples of the commercially available reduced coenzyme oxidase include NADH oxidase (made by Cosmo Bio Co., Ltd.).

The concentration of the reduced coenzyme oxidase used in the method for measuring SM according to the present invention in the reaction solution is not particularly limited as long as it is a concentration which enables the measurement of SM according to the present invention; it is generally 0.01 to 400,000 U/L, preferably 0.02 to 200,000 U/L.

The catalase used in the method for measuring SM according to the present invention is not particularly limited as long as it is an enzyme capable of concerting hydrogen peroxide so water and an oxygen molecule; there can alto be used, for example, a catalase derived from an animal, a plant, or a microorganism as well as a catalase produced by a genetic engineering technique. The catalase may also be a commercially available one. Examples of the commercially available catalase include Catalase (CAT made by KikKoman Corporation), Catalase (CAT-R made by Kikkoman Corporation), and Catalase derived from bovine liver (made by Sigma-Aldrich Corporation). In the present invention, a combination of two or more catalases can also be used.

The concentration of the catalase used in the method for measuring SM according to the present invention in the reaction solution is not particularly limited as long as it is a concentration which enables the measurement of SM according to the present invention; it is generally 0.001 to 1,000,000 U/L, preferably 0.01 to 500,000 U/L.

The aqueous medium used in the present invention is not particularly limited as long as it is an aqueous medium which enables the method for measuring SM according to the present invention; examples thereof include deionized water, distilled water, and a buffer solution. Among them, a buffer solution is preferable. Examples of the buffer used in the buffer solution include a tris(hydroxymethyl)aminomethane buffer, a phosphate buffer, a boric-acid buffer, and a Good's buffer.

Examples of the Good's buffer include 2-morpholinoethanesulfonic acid (MES), bis(2-hydroxyethyl)iminotris(hydroxymethyl)methane (Bis-Tris), N-(2-acetamido)iminodiacetate (ADA), piperazine-N,N'-bis(2-ethanesulfonic acid) (PIPES), N-(2-acetamido)-2-aminoethanesulfonic acid (ACES), 3-morpholino-2-hydroxypropanesulfonic acid (MOPSO), N,N-bis(2-hydroxyethyl)-2-aminoethanesulfonic acid (BES), 3morpholinopropanesulfonic acid (MOPS), N-[tris(hydroxymethyl)methyl]-2-aminoethanesulfonic acid (TES), 2-[4-(2-hydroxyethyl)-1-piperazinyl]ethanesulfonic acid (HEPES), 3-[N,N-bis(2-hydroxyethyl)amino]-2-hydroxypropanesulfonic acid (DIPSO), N-[tris(hydroxymethyl)methyl]-2-hydroxy-3-aminopropanesulfonic acid (TAPSO), piperazine-N,N'-bis(2-hydroxypropanesulfonic acid) (POPSO), 3-[4-(2-hydroxyethyl)-1-piperazinyl]-2-hydroxypropanesulfonic acid (HEPPSO), 3-[4-(2-hydroxyethyl)-1-piperazinyl]propanesulfonic acid [(H)EPPS], N-[tris(hydroxymethyl)methyl]glycine (Tricine), N,N-bis(2-hydroxyethyl)glycine (Bicine), N-tris(hydroxymethyl)methyl-3-aminopropanesulfonic acid (TAPS), N-cyclohexyl-2-aminoethanesulfonic acid (CHES), N-cyclohexyl-3-amino-2-hydroxypropanesulfonic acid (CAPSO), and N-cyclohexyl-3-aminopropanesulfonic acid (CAPS). The concentration of the buffer solution is not particularly limited as long as it is a concentration suitable for measurement, and it is generally 0.001 to 2.0 moles/L, preferably 0.005 to 1.0 moles/L.

The peroxidase used in the present invention is not particularly limited as long as it is a peroxidase which enables the method for measuring SM according to the present invention; examples thereof include a peroxidase derived from horseradish.

The concentration of the peroxidase used in the method for measuring SM according to the present invention in the reaction solution is not particularly limited as long as it is a concentration which enables the measurement of SM according to the present invention; it is generally 0.01 to 500,000 U/L, preferably 1 to 200,000 U/L.

The leuco chromogen used in the method for measuring SM according to the present invention is not particularly limited as long as it is a leuco chromogen which enables the method for measuring SM according to the present invention. The leuco chromogen has the function of forming a dye by itself by reacting with hydrogen peroxide in the presence of a peroxidase.

Examples of the leuco chromogen include 10-N-carboxymethylcarbamoyl-3,7-bis(dimethylamino)-10H-phenothiazine (CCAP), 10-N-nmethylcarbamoyl-3,7-bis(dimethylamino)10H-phenothiazine (MCDP), sodium N-(carboxymethylaminocarbonyl)-4,4'-bis(dimethylamino) diphenylamine (DA-64), sodium 10-N-carboxymethylaminocarbonyl)-3,7-bis(dimethylamino-10H-phenothiazine (DA-67), 4,4'-bis(dimethylamino)diphenylamine, and bis[3-bis(4-chlorophenyl)methyl-4-dimethylaminophenyl]amine (BCMA).

The concentration of the leuco chromogen used in the method for measuring SM according to the present invention in the reaction solution is not particularly limited as long as it is a concentration which enables the measurement of SM according to the present invention; it is generally 0.001 to 5 g/L, preferably 0.01 to 1 g/L.

The oxidative coupling-coloring chromogen used in the method for measuring SM according to the present invention is not particularly limited as long as it is an oxidative coupling-coloring chromogen which enables the method for measuring SM according to the present invention. The oxidative coupling-coloring chromogen has the function of forming a dye by reacting with hydrogen peroxide in the presence of a peroxidase. A combination of a pair of oxidative coupling-coloring chromogens is used in the reaction of forming a dye. The oxidative coupling-coloring chromogen also has the function of converting hydrogen peroxide to a colorless substance by reacting with the hydrogen peroxide in the presence of a peroxidase. Only one of the pair of oxidative coupling-coloring chromogens is used in the reaction of converting hydrogen peroxide to a colorless substance. Examples of the combination composed of a pair of oxidative coupling-coloring chromogens include a combination of a coupler and an aniline and a combination of a coupler and a phenol.

Examples of the coupler include 4-aminoantipyrine (4-AA) and 3-methyl-2-benzothiazolinone hydrazine.

Examples of the aniline include N-(3-sulfopropyl)aniline, N-ethyl-N-(2-hydroxy-3-sulfopropyl)-3-methylaniline (TOOS), N-ethyl-N-(2-hydroxy-3-sulfopropyl)-3,5-dimethylaniline (MAOS), N-ethyl-N-(2-hydroxy-3-sulfopropyl)-3,5-dimethoxyaniline (DAOS), N-ethyl-N-(3-sulfopropyl)-3-methylaniline (TOPS), N-(2-hydroxy-3-sulfopropyl)-3,5-dimethoxyaniline (HDAOS), N,N-dimethyl-3-methylaniline, N,N-di(3-sulfopropyl)-3,5-dimethoxyaniline, N-ethyl-N-(3-sulfopropyl-3-methoxyaniline, N-ethyl-N-(3-sulfopropyl)aniline, N-ethyl-N-(3-sulfopropyl)-3,5-dimethoxyaniline, N-(3-sulfopropyl)-3,5-dimethoxyaniline, N-ethyl-N-(3-sulfopropyl)-3,5-methoxyaniline, N-ethyl-N-(2-hydroxy-3-sulfopropyl)-3-methoxyaniline, N-ethyl-N-(2-hydroxy-3-sulfopropyl)aniline, N-ethyl-N-(3-methylphenyl)-N'-succinylethylenediamine (EMSE), N-ethyl-N-(3-methylphenyl-N'-acetylethylenediamine, and N-ethyl-N-(2-hydroxy-3-sulfopropyl)-4-fluoro-3,5-dimethoxyaniline (F-DAOS).

Examples of the phenol include phenol, 4-chlorophenol, 3-methylphenol, and 3-hydroxy-2,4,6-triiodobenzoic acid (HTIB).

The concentration of the oxidative coupling-coloring chromogen used in the method for measuring SM according to the present invention in the reaction solution is not particularly limited as long as it is a concentration which enables the measurement of SM according to the present invention; it is generally 0.001 to 5 g/L, preferably 0.01 to 1 g/L.

<Kit for Measuring SM>

The kit for measuring SM according to the present invention is used for the method for measuring SM according to the present invention. Examples of the kit for measuring SM according to the present invention include a two-reagent system kit and a three-reagent system kit, and preferred is a two-reagent system kit consisting of a first reagent and a second reagent.

The kit for measuring SM according to the present invention may be in a freeze-dried state or a state dissolved in an aqueous medium. In case the kit in a freeze-dried state is used to measure SM in a sample, it is dissolved in an aqueous medium before measurement and then used. Examples of the aqueous medium include the aforementioned aqueous media.

In the kit for measuring SM according to the present invention, those aforementioned phospholipase D which does not react with SM and LPS but reacts with PC, lysophospholipase or monoglyceride lipase, choline oxidase, phospholipase D which does not react with glycerol-3-phosphorylcholine and free fatty acid but reacts with SM, oxidized coenzyme, choline dehydrogenase, reduced coenzyme oxidase, catalase, catalase inhibitor, leuco chromogen, and oxidative coupling-coloring chromogen can be used.

In a two-reagent system kit for measuring SM consisting of a first reagent and a second reagent, the phospholipase D which does not react with SM and LPC but reacts wish PC is contained in the first reagent. The lysophospholipase or the monoglyceride lipase is contained in the first reagent. The phospholipase D which does not react with glycerol-3-phosphorylcholine and free fatty acid but reacts with SM is contained in the second reagent. The choline oxidase is contained in the first reagent, and it may further be contained in the second reagent. The choline dehydrogenase is contained in the first reagent, and it may further be contained in the second reagent. The oxidized coenzyme is contained in the first reagent, and it may further be contained in the second reagent. The reduced coenzyme oxidase is contained in the first reagent, and it may further be contained in the second reagent. The catalase is contained in the first reagent. The catalase inhibitor is contained in the second reagent. The peroxidase is contained in the first reagent, and it may further be contained in the second reagent. The leuco chromogen is contained in the second reagent. In case hydrogen peroxide is eliminated in the presence of a peroxidase and one of the pair of oxidative coupling-coloring chromogens, one of the pair of oxidative coupling-coloring chromogens is contained in the first reagent. In case hydrogen peroxide is measured in the presence of a peroxidase and the pair of oxidative coupling-coloring chromogens, an embodiment wherein one of the pair of oxidative coupling-coloring chromogens is contained in the first reagent, and the other or the pair of oxidative coupling-coloring chromogens is contained in the second reagent, respectively, is preferred.

In the kit for measuring SM according to the present invention, the concentration of the phospholipase D which does not react with SM and LPC but reacts with PC in the first reagent is generally 0.002 to 400,000 U/L, preferably 0.01 to 200,000 U/L. In the kit for measuring SM in a freeze-dried state, the content of the phospholipase D which does not react with SM and LPC but reacts with PC in the first reagent is such a content that the concentration thereof in a state dissolved in an aqueous medium is generally 0.002 to 400,000 U/L, preferably 0.01 to 200,000 U/L.

In the kit for measuring SM according to the present invention, the concentration of the lysophospholipase or the monoglyceride lipase in the first reagent is generally 0.002 to 400,000 U/L, preferably 0.01 to 200,000 U/L. In the kit for measuring SM in a freeze-dried state, the content of the lysophospholipase or the monoglyceride lipase in the first reagent is such a content that the concentration thereof in a state dissolved in an aqueous medium is generally 0.002 to 400,000 U/L, preferably 0.01 to 200,000 U/L.

In the kit for measuring SM according to the present invention, the concentration of the choline oxidase in the first reagent is generally 0.002 to 400,000 U/L, preferably 0.01 to 200,000 U/L. In the kit for measuring SM in a freeze-dried state, the content of the choline oxidase in the first reagent is such a content that the concentration thereof in a state dissolved in an aqueous medium is generally 0.002 to 400,000 U/L, preferably 0.01 to 200,000 U/L.

In the kit for measuring SM according to the present invention, the concentration of the phospholipase D which does not react with glycerol-3-phosphorylcholine and free fatty acid but reacts with SM in the second reagent is generally 0.004 to 800,000 U/L, preferably 0.02 to 400,000 U/L. In the kit for measuring SM in a freeze-dried state, the content of the phospholipase D which does not react with glycerol-3-phosphorylcholine and free fatty acid but reacts with SM in the second reagent is such a content that the concentration thereof in a state dissolved in an aqueous medium is generally 0.004 to 800,000 U/L, preferably 0.02 to 400,000 U/L.

In the kit for measuring SM according to the present invention, the concentration of the choline dehydrogenase in the first reagent is generally 0.002 to 400,000 U/L, preferably 0.01 to 200,000 U/L. In the kit for measuring SM in a freeze-dried state, the content of the choline dehydrogenase in the first reagent is such a content that the concentration thereof in a state dissolved in an aqueous medium is generally 0.002 to 400,000 U/L, preferably 0.01 to 200,000 U/L.

In the kit for measuring SM according to the present invention, the concentration of the oxidized coenzyme in the first reagent is generally 0.02 to 800 mmoles/L, preferably 0.2 to 200 mmoles/L. In the kit for measuring SM in a freeze-dried state, the content of the oxidized coenzyme in the first reagent is such a content that the concentration thereof in a state dissolved in an aqueous medium is generally 0.02 to 800 mmoles/L, preferably 0.2 to 200 mmoles/L.

In the kit for measuring SM according to the present invention, the concentration of the reduced coenzyme oxidase in the first reagent is generally 0.02 to 800,000 U/L, preferably 0.04 to 400,000 U/L. In the kit for measuring SM in a freeze-dried state, the content of the reduced coenzyme oxidase in the first reagent is such a content that the concentration thereof in a state dissolved in an aqueous medium is generally 0.02 to 800,000 U/L, preferably 0.04 to 400,000 U/L.

In the kit for measuring SM according to the present invention, the concentration of the catalase in the first reagent is generally 0.002 to 1,500,000 U/L, preferably 0.02 to 750.000 U/L. In the kit for measuring SM in a freeze-dried state, the content of the catalase in the first reagent is such a content that the concentration thereof in a state dissolved in an aqueous medium is generally 0.002 to 1,500,000 U/L, preferably 0.02 to 750,000 U/L.

In the kit for measuring SM according to the present invention, the concentration of the peroxidase in the first reagent is generally 0.01 to 500,000 U/L, preferably 1 to 200,000 U/L. In the kit for measuring SM in a freeze-dried state, the content of the peroxidase in the first reagent is such a content that the concentration thereof in a state dissolved in an aqueous medium is generally 0.01 to 500,000 U/L, preferably 1 to 200,000 U/L.

In the kit for measuring SM according to the present invention, the concentration of the leuco chromogen in the second reagent is generally 0.002 to 7.5 g/L, preferably 0.02 to 1.5 g/L. In the kit for measuring SM in a freeze-dried state, the content of the leuco chromogen in the second reagent is such a content that the concentration thereof in a state dissolved in an aqueous medium is generally 0.002 to 7.5 g/L, preferably 0.02 to 1.5 g/L.

In the kit for measuring SM according to the present invention, the concentration of tire oxidative coupling-coloring chromogen in each of the first reagent and the second reagent is generally 0.002 to 7.5 g/L, preferably 0.02 to 1.5 g/L, In the kit for measuring SM in a freeze-dried state, the content of the oxidative coupling-coloring chromogen in each of the first reagent and the second reagent is such a content that the concentration thereof in a state dissolved in an aqueous medium is generally 0.002 to 7.5 g/L, preferably 0.02 to 1.5 g/L.

The kit for measuring SM according to the present invention may comprise an aqueous medium, a stabilizer, a preservative, an agent suppressing the influence of an interference substance, a reaction promoter, or a surfactant, if necessary. Examples of the aqueous medium include the aforementioned aqueous media. Examples of the stabilizer include ethylenediaminetetraacetic acid (EDTA), sucrose, calcium chloride, glycine, sodium glutamate, and tryptophan. Examples of the preservative include sodium azide, an antibiotic, and BioAce. Examples of the agent suppressing the influence of an interference substance include an ascorbate oxidase for suppressing the influence of ascorbic acid and a ferrocyanide for suppressing the influence of bilirubin. Examples of the reaction promoter include an enzyme such as colipase and a salt such as sodium sulfate and sodium chloride. Examples of the surfactant include a non-ionic surfactant, a cationic surfactant, an anionic surfactant, and an amphoteric surfactant. Examples of the non ionic surfactant include a polyoxyethylene surfactant.

Specific embodiments of the kit for measuring SM according to the present invention will be described below. However, the kit for measuring SM according to the present invention is not limited thereto.

Kit 1

First Reagent

A phospholipase D which does not react with SM and LPC but reacts with PC; a lysophospholipase or a monoglyceride lipase; a choline oxidase; a catalase; and a peroxidase Second Reagent A phospholipase D which does not react with glycerol-3-phosphorylcholine and free fatty acid but reacts wish SM; a catalase inhibitor; and a leuco chromogen Kit 2

First Reagent

A phospholipase D which does not react with SM and LPC but reacts with PC; a lysophospholipase or a monoglyceride lipase; a choline oxidase; a catalase; and a peroxidase Second Reagent A phospholipase D which does not react with glycerol-3-phosphorylcholine and free fatty acid but reacts with SM; a choline oxidase; a catalase inhibitor; and a leuco chromogen Kit 3

First Reagent

A phospholipase D which does not react with SM and LPC but reacts with PC; a lysophospholipase or a monoglyceride lipase; a choline dehydrogenase; an oxidized coenzyme; a reduced coenzyme oxidase; a catalase; and a peroxidase Second Reagent A phospholipase D which does not react with glycerol-3-phosphorylcholine and free fatty acid but reacts with SM; a catalase inhibitor; and a leuco chromogen Kit 4

First Reagent

A phospholipase D which does not react with SM and LPS but reacts with PC; a lysophospholipase or a monoglyceride lipase; a choline dehydrogenase; an oxidized coenzyme; a reduced coenzyme oxidase; a catalase; and a peroxidase Second Reagent A phospholipase D which does not react with glycerol-3-phosphorylcholine and free fatty acid but reacts with SM; a choline dehydrogenase; an oxidized coenzyme; a reduced coenzyme oxidase; a catalase inhibitor; and a leuco chromogen Kit 5

First Reagent

A phospholipase D which does not react with SM and LPS but reacts with PC; a lysophospholipase or a monoglyceride lipase; a choline oxidase; a peroxidase; and one of a pair of oxidative coupling-coloring chromogens Second Reagent A phospholipase D which does not react with glycerol-3-phosphorylcholine and free fatty acid but reacts with SM; and the other of the pair of oxidative coupling-coloring chromogens Kit 6

First Reagent

A phospholipase D which does not react with SM and LPC but reacts with PC; a lysophospholipase or a monoglyceride lipase; a choline oxidase; a peroxidase; and one of a pair of oxidative coupling-coloring chromogens Second Reagent A phospholipase D which does not react with glycerol-3-phosphorylcholine and free fatty acid but reacts with SM; a choline oxidase; and the other of the pair of oxidative coupling-coloring chromogens Kit 7

First Reagent

A phospholipase D which does not react with SM and LPC but reacts with PC; a lysophospholipase or a monoglyceride lipase; a choline dehydrogenase; an oxidized coenzyme; a reduced coenzyme oxidase; a peroxidase; and one of a pair or oxidative coupling-coloring chromogens Second Reagent A phospholipase D which does not react with glycerol-3-phosphorylcholine and free fatty acid but reacts with SM; and the other of the pair of oxidative coupling-coloring chromogens Kit 8

First Reagent

A phospholipase D which does not react with SM and LPC but reacts with PC; a lysophospholipase or a monoglyceride lipase; a choline dehydrogenase; an oxidized coenzyme; a reduced coenzyme oxidase; a peroxidase; and one of a pair of oxidative coupling-coloring chromogens Second Reagent A phospholipase D which does not react with glycerol-3-phosphorylcholine and free fatty acid but reacts with SM; a choline dehydrogenase; an oxidized coenzyme; a reduced coenzyme oxidase; and the other of the pair of oxidative coupling-coloring chromogens Kit 9

First Reagent

A phospholipase D which does not react with SM and LPC but reacts with PC; a lysophospholipase or a monoglyceride lipase; a choline oxidase; a peroxidase; and one of a pair of oxidative coupling-coloring chromogens Second Reagent A phospholipase D which does not react with glycerol-3-phosphorylcholine and free fatty acid but reacts with SM; a peroxidase; and the other of the pair of oxidative coupling-coloring chromogens Kit 10

First Reagent

A phospholipase D which does not react with SM and LPC but reacts with PC; a lysophospholipase or a monoglyceride lipase; a choline oxidase; a peroxidase; and one of a pair of oxidative coupling-coloring chromogens Second Reagent A phospholipase D which does not react with glycerol-3-phosphorylcholine and free fatty acid but reacts with SM; a choline oxidase; a peroxidase; and the other of the pair of oxidative coupling-coloring chromogens Kit 11

First Reagent

A phospholipase D which does not react with SM and LPC but reacts with PC; a lysophospholipase or a monoglyceride lipase; a choline dehydrogenase; an oxidized coenzyme; a reduced coenzyme oxidase; a peroxidase; and one of a pair of oxidative coupling-coloring chromogens Second Reagent A phospholipase D which does not react with glycerol-3-phosphorylcholine and free fatty acid but reacts with SM; a peroxidase; and the other of the pair of oxidative coupling-coloring chromogens Kit 12

First Reagent

A phospholipase D which does not react with SM and LPC but reacts with PC; a lysophospholipase or a monoglyceride lipase; a choline dehydrogenase; an oxidized coenzyme; a reduced coenzyme oxidase; a peroxidase; and one of a pair of oxidative coupling-coloring chromogens Second Reagent A phospholipase D which does not react with glycerol-3-phosphorylcholine and free fatty acid but reacts with SM; a choline dehydrogenase; an oxidized coenzyme; a reduced coenzyme oxidase; a peroxidase; and the other of the pair of oxidative coupling-coloring chromogens The present invention well be described below in further detail with reference to Examples, which are not intended in any way to limit the scope of the present invention. In these Examples and Reference Examples, reagents and enzymes from the following manufacturers were used.

PIPES (made by Dojindo Co., Ltd.), EMSE (made by Daito Chemix Corporation, calcium chloride dihydrate (made by Wake Pure Chemical Industries, Ltd.), 4-AA (made by Saikyo Kasei Co., Ltd.), peroxidase (POD made by Toyobo Co., Ltd.) catalase (made by Kikkoman Corporation), CLOD (choline oxidase made by Kyowa Hakko Co., Ltd.) sodium azide (made by Wake Pure Chemical Industries, Ltd.), MGLP (monoglyceride lipase made by Asahi Kasei Corporation), PLDP (made by Asahi Kasei Corporation), PLD (made by Asahi Kasei Corporation), phosphatidylcholine (made by Sigma-Aldrich Corporation), lysophosphatidylcholine (made by Sigma-Aldrich Corporation), SM (made by Sigma-Aldrich Corporation), and Triton X-100 (polyoxyethylene surfactant made by Sigma-Aldrich Corporation).

EXAMPLE 1

The reactivity of each of the phospholipids of PC, LPC, and SM, to enzymes, (1) PLDP, (2) PLD, and (3) MGLP, was evaluated by the following method.

<Kit>

Kits (kits A to F) consisting of the following first and second reagents as shown in Table 3 were prepared.

First Reagent

| | |
|---|---|
| PIPES (pH 7.0) | 15 g/L |
| EMSE | 0.3 g/L |
| Triton X-100 | 0.05 g/L |
| MGLP | |

Second Reagent

| | |
|---|---|
| PIPES (pH 7.5) | 15 g/L |
| 4-AA | 0.5 g/L |
| Sodium azide | 0.2 g/L |
| POD | 20 kU/L |
| Calcium chloride dihydrate | 0.3 g/L |
| CLOD | 30 kU/L |
| PLDP or PLD | |

TABLE 3

| | First Reagent | | Second Reagent | |
|---|---|---|---|---|
| Kit | Enzyme | Concentration | Enzyme | Concentration |
| Kit A | None | — | None | — |
| Kit B | None | — | PLDP | 30 kU/L |
| Kit C | None | — | PLD | 4 kU/L |
| Kit D | MGLP | 10 kU/L | None | — |
| Kit E | MGLP | 10 kU/L | PLDP | 30 kU/L |
| Kit F | MGLP | 10 kU/L | PLD | 4 kU/L |

<Sample>

A saline solution, an SM standard solution (SM concentration: 100 mg/dL), a PC standard solution (PC concentration: 100 mg/dL), and an LPC standard solution (LPC concentration: 100 mg/dL) were used as samples.

<Measurement Using Kit A—Absorbance for Standard Solution>

"Absorbance" for the SM standard solution was determined by the following method on a Hitachi 7170S autoanalyzer using the saline solution (phospholipid: 0.0 mg/dL) and the SM standard solution as samples and Kit A as a kit.

The saline solution (2.5 µL) and the first reagent (240 µL) were added to a reaction cell and incubated at 37° C. for 5 minutes; the absorbance ($E1_{saline\ solution}$) of the reaction solution was measured at a main wavelength of 600 nm and a sub-wavelength of 700 nm; the second reagent (80 µL) was then added to this reaction solution, which was further incubated at 37° C. for 5 minutes; and the absorbance ($E2_{saline\ solution}$) of the reaction solution was measured at a main wavelength of 600 nm and a sub-wavelength of 700 nm. The value obtained by subtracting $E1_{saline\ solution}$ from $E2_{saline\ solution}$ was defined as $\Delta E_{saline\ solution}$.

The same reaction as described above except for using the SM standard solution in place of the saline solution as a sample was performed; $E1_{SM}$ was subtracted from $E2_{SM}$; and the resultant was defined as $\Delta E_{SM}$. As shown in Equation (I), the value obtained by subtracting the above $\Delta E_{saline\ solution}$ from $\Delta E_{SM}$ was defined as "absorbance" (A) for the SM standard solution.

[Equation 1]

$$\text{"Absorbance" (A) for SM standard solution} = \Delta E_{SM} - \Delta E_{saline\ solution} \quad (I)$$

"Absorbance" (A) for the PC standard solution and "absorbance" (A) for the LPC standard solution ware determined, in the same way except for using the PC standard solution and the LPC standard solution, respectively, in place of the SM standard solution.

<Measurement Using Kits B to F—Absorbance for Standard Solutions>

Using each of the Kits B to F in place of Kit A, "absorbance" for each of the standard solutions in each of the Kits was determined. The "absorbance" for each of the standard solutions in each of the Kits is shown in FIG. 1.

Figure 1:
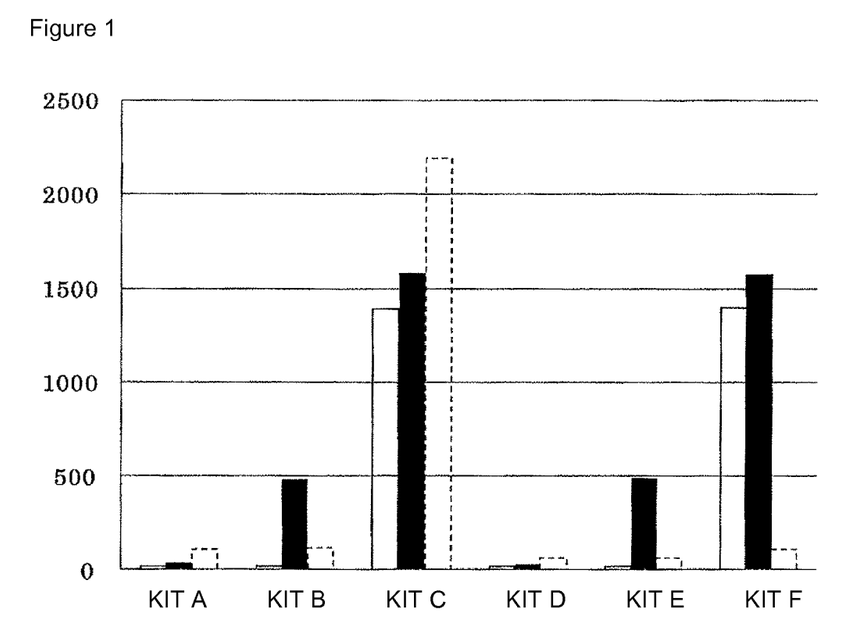
FIG. 1 is a graph showing "absorbance" for each of the standard solutions of phospholipids or SM, LPC, and PC, in the kits (kits A to F) of Example 1. The vertical axis represents absorbance (mAbs) and the horizontal axis represents the kits (kits A to F). The while bar indicates SM; the black bar indicates PC; and the dotted frame bar indicates LPC.

The following were revealed from FIG. 1. First, in case Kit A was used, none of the phospholipids reacts with the choline oxidase since "absorbance" was undetectable for any of the phospholipids. It was shown from the reaction using Kit B that PLDP specifically reacted with PC to form choline. It was shown from the reaction using Kit C that PLD reacted with each of the phospholipids to form choline.

It was shown from the reaction using Kit D that none of the phospholipids formed choline by reaction with MGLP.

In case Kit E was used, it was shown that only PC react form choline. From comparison of this with the reaction using Kit B, it was considered that PC did not react with MGLP but reacted with PLDP to form choline. Because "absorbance" was undetectable for LPC, it proved that glycerol-3-phosphorylcholine and free fatty acid formed by the reaction of LPC with MGLP did not react with PLDP and did not form choline.

It was shown from the reaction using Kit F that choline was formed from PC and SM. From comparison of this with the reaction using Kit C, it was considered that PC and SM did not react with MGLP but reacted with PLD to form choline. On the other hand, because "absorbance" was undetectable for LPC, it proved that glycerol-3-phosphorylcholine and free fatty acid formed by the reaction of LPC with MGLP and did not react with PLD and did not form choline.

Thus, the followings were found. By acting PLDP on a sample comprising PC, LPC, and SM, only PC reacted with PLDP, and the formed choline was eliminated by converting the choline to hydrogen peroxide; subsequently, by acting of MGLP on the remaining LPC and SM, and then acting of PLD thereon, only SM in the sample reacted with PLD to form choline, because only LPC reacted with MGLP to form glycerol-3-phosphorylcholine and free fatty acid, both of which did not react with PLD; and consequently, only SM could be measured by measuring the hydrogen peroxide formed from the choline.

EXAMPLE 2

A kit for measuring SM consisting of the following first and second reagents was prepared.

First Reagent

| | |
|---|---|
| PIPES (pH 6.25) | 15 g/L |
| EMSE | 0.3 g/L |
| Catalase | 300 kU/L |
| PLDP | 10 kU/L |
| MGLP | 10 kU/L |
| CLOD | 10 kU/L |
| Triton X-100 | 0.05 g/L |

Second Reagent

| | |
|---|---|
| PIPES (pH 7.5) | 15 g/L |
| 4-AA | 0.5 g/L |
| Sodium azide | 0.2 g/L |
| POD | 20 kU/L |
| PLD | 4 kU/L |
| CLOD | 10 kU/L |
| Calcium chloride dihydrate | 0.3 g/L |
| Triton X-100 | 8 g/L |

EXAMPLE 3

Using the measurement kit of Example 2 and Sphingomyelin Assay Kit (made by Cayman Chemical Company) as a control kit, the concentration of SM in each of 28 human serum samples was determined by the following procedure.

(1) Preparation of Calibration Curve

A calibration curve showing the relationship between the SM concentration and the "absorbance" was prepared by measurement on a Hitachi 7170S autoanalyzer using the kit of Example 2 as a kit as well as a saline solution (SM: 0.0 mg/dL) and a standard serum with a SM concentration of 35.0 mg/dL as standard solutions.

The "absorbance" described here means to describe a value obtained by subtracting E1 from E2 based on two absorbances (E1 and E2) measured by the following reactions.

The standard solution (2.5 μL) and the first reagent (240 μL) were added to a reaction cell and incubated at 37° C. for 5 minutes; the absorbance (E1) of the reaction solution was measured at a main wavelength of 600 nm and a sub-wavelength of 700 nm; the second reagent (80 μL) was then added to this reaction solution, and the mixture was further incubated at 37° C. for 5 minutes; and the absorbance (E2) of the reaction solution was measured at a main wavelength of 600 nm and a sub-wavelength of 700 nm.

(2) Measurement of "Absorbance" for Human Serum Sample

"Absorbance" for each of the human serum samples (28 samples) was measured by performing the same operation as in the "absorbance" calculation method of (1) except for using each of the samples in place of each of the standard solutions in the preparation of calibration curve of (1).

(3) Determination of Concentration of SM in Human Serum Sample

The concentration of SM in each of the samples was determined from the "absorbance" measured in (2) and the calibration curve prepared in (1).

(4) Determination of Concentration of SM Using Control Kit

According to the instructions for the control kit, the control kit was used to determine the concentration of SM in each of the same 28 human serum samples.

Figure 2:
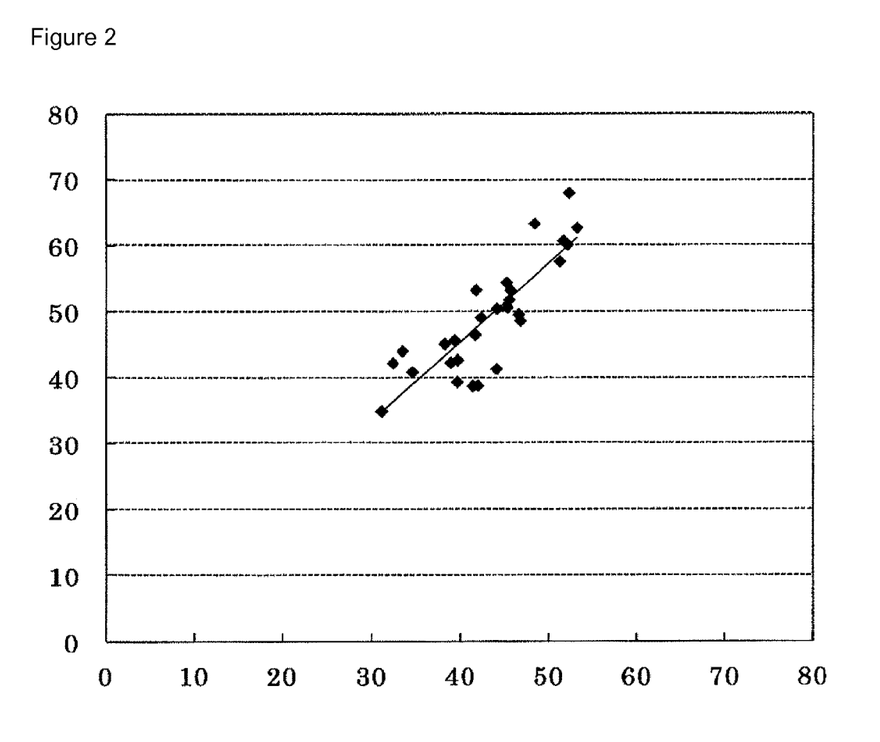
FIG. 2 is a graph showing a correlation chart between measurements using the kit of Example 2 and using a control kit. The vertical axis represents the concentration (mg/dL) of SM in a sample, determined by the measurement using the kit of Example 2, and the horizontal axis represents the concentration (mg/dL) of SM in a sample, determined by the measurement using the control kit.

The correlation between measurements using the control kit and those using the kit of Example 2 was evaluated from the SM concentration (x) in each of the samples determined by the measurement using the control kit and the SM concentration (y) in each of the samples determined by the measurement using the kit of Example 2; as a result, the correlation chart shown in FIG. 2 was obtained. This correlation chart showed chat the relationship of Equation (II) was established between x and y with the correlation coefficient (r) of 0.8445, which reveals that a good correlation exists between both measurements.

[Equation 2]

$$y = 1.1911 * x - 2.2176 \quad (II)$$

EXAMPLE 4

An SM standard solution (SM concentration: 100 mg/dL) was used to prepare a 10-fold serial dilution, and absorbance was measured for each of the diluted samples by the same method as in Example 3. The results are shown in FIG. 3.

Figure 3:
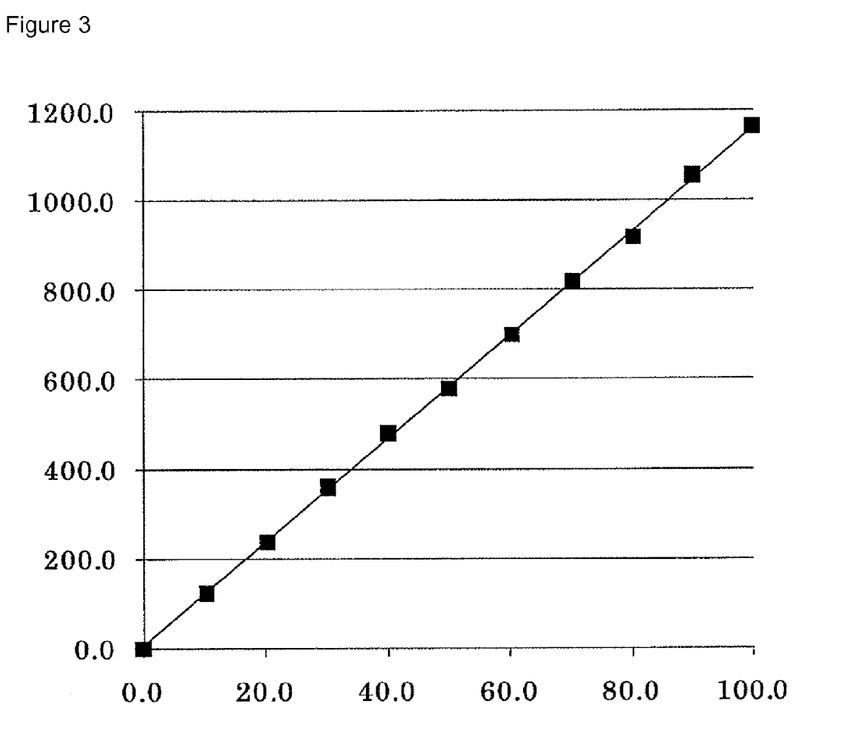
FIG. 3 is a graph showing the relationship between the SM concentration and the absorbance in the measurement using the kit of Example 2. The vertical axis represents the absorbance (mAbs), and the horizontal axis represents the SM concentration (mg/dL).

FIG. 3 showed that the measurement using the kit or Example 2 provided an extremely good linearity between the SM concentration and the absorbance.

EXAMPLE 5

The kit of Example 2 was used to evaluate specificity for SM. As samples, a saline solution, an SM standard solution (SM concentration: 100 mg/dL), a PC standard solution (PC concentration: 100 mg/dL), and an LPC standard solution (LPC concentrations: 100 mg/dL) were used to measure "absorbance" for each of the samples by the method of Example 3.

As a kit for measuring phospholipids, "Determiner L PL" (manufactured by Kyowa Medex Co., Ltd.) was used in place of the kit of Example 2 to measure "absorbance" for each of the samples by the same method as in Example 3. The measurement results are shown in Table 4.

TABLE 4

| | Absorbance (mAbs) | |
|---|---|---|
| | Example 2 | Determiner L PL |
| Saline Solution | 0.0 | 0.0 |
| SM(SM) | 136.1 | 139.0 |
| Phosphatidylcholine (PC) | 2.7 | 141.0 |
| Lysophosphatidylcholine (LPC) | 5.4 | 198.2 |

As shows in Table 4, all phospholipids of SM, PC, and LPC, reacted in the measurement using "Determiner L PL" while only SM reacted in the measurement using the kit of Example 2. Thus, the kit of Example 2 was confirmed to be a kit for specifically measuring SM.

Industrial Applicability

According to the present invention, a method and a kit for measuring SM in the blood useful for diagnosis of arteriosclerosis and the like are provided.

The invention claimed is:

1. A method for measuring sphingomyelin in a sample, comprising
reacting the sample with a phospholipase D which does not react with sphingomyelin and lysophosphatidylcholine but reacts with phosphatidylcholine; a lysophospholipase or a monoglyceride lipase; and a choline oxidase,
eliminating the formed hydrogen peroxide,
reacting the resultant with a phospholipase D which does not react with glycerol-3-phosphorylcholine and free fatty acid but reacts with sphingomyelin; and a choline oxidase,
measuring the formed hydrogen peroxide, and
correlating the formed hydrogen peroxide with a calibration curve to determine sphingomyelin in the sample.

2. A method for measuring sphingomyelin in a sample, comprising
reacting the sample with a phospholipase D which does not react with sphingomyelin and lysophosphatidylcholine but reacts with phosphatidylcholine; a lysophospholipase or a monoglyceride lipase; an oxidized coenzyme; a choline dehydrogenase; and a reduced coenzyme oxidase,
eliminating the formed hydrogen peroxide,
reacting the resultant with a phospholipase D which does not react with glycerol-3-phosphorylcholine and free fatty acid but reacts with sphingomyelin; an oxidized coenzyme; a choline dehydrogenase; and a reduced coenzyme oxidase,
measuring the formed hydrogen peroxide, and
correlating the formed hydrogen peroxide with a calibration curve to determine sphingomyelin in the sample.

3. The method according to claim 1, wherein the reaction of the sample with the phospholipase D which does not react with sphingomyelin and lysophosphatidylcholine but reacts with phosphatidylcholine, the lysophospholipase or the monoglyceride lipase, and the choline oxidase is performed in the presence of a catalase, and the reaction of the resultant with the phospholipase D which does not react with glycerol-3-phosphorylcholine and free fatty acid but reacts with sphingomyelin, and the choline oxidase is performed in the presence of a catalase inhibitor.

4. The method according to claim 2, wherein the reaction of the sample with the phospholipase D which does not react with sphingomyelin and lysophosphatidylcholine but reacts with phosphatidylcholine, the lysophospholipase or the monoglyceride lipase, the oxidized coenzyme, the choline dehydrogenase, and the reduced coenzyme oxidase is performed in the presence of a catalase, and the reaction of the resultant with phospholipase D which does not react with glycerol-3-phosphorylcholine and free fatty acid but reacts with sphingomyelin, the oxidized coenzyme, the choline dehydrogenase, and the reduced coenzyme oxidase is performed in the presence of a catalase inhibitor.

5. The method according to claim 3, wherein the catalase inhibitor is an azide.

6. The method according to claim 1, wherein the eliminating of hydrogen peroxide is performed in the presence of a peroxidase and one of a pair of oxidative coupling-coloring chromogens, and the measurement of hydrogen peroxide is performed in the presence of the peroxidase and the pair of oxidative coupling-coloring chromogens.

7. The method according to claim 1, wherein the measurement of hydrogen peroxide is performed in the presence of a peroxidase and a leuco chromogen.

8. The method according to claim 1, wherein the phospholipase D which does not react with sphingomyelin and lysophosphatidylcholine but reacts with phosphatidylcholine is a phospholipase D derived from *Streptomyces* sp.

9. The method according to claim 1, wherein the phospholipase D which does not react with glycerol-3-phosphorylcholine and free fatty acid but reacts with sphingomyelin is a phospholipase D derived from *Streptomyces chromofuscus*.

10. The method according to claim 4, wherein the catalase inhibitor is an azide.

11. The method according to claim 2, wherein the eliminating of hydrogen peroxide is performed in the presence of a peroxidase and one of a pair of oxidative coupling-coloring chromogens, and the measurement of hydrogen peroxide is performed in the presence of the peroxidase and the pair of oxidative coupling-coloring chromogens.

12. The method according to claim 2, wherein the measurement of hydrogen peroxide is performed in the presence of a peroxidase and a leuco chromogen.

13. The method according to claim 2, wherein the phospholipase D which does not react with sphingomyelin and lysophosphatidylcholine but reacts with phosphatidylcholine is a phospholipase D derived from *Streptomyces* sp.

14. The method according to claim 2, wherein the phospholipase D which does not react with glycerol-3-phosphorylcholine and free fatty acid but reacts with sphingomyelin is a phospholipase D derived from *Streptomyces chromofuscus*.

15. The method according to claim 1, wherein the reaction of the sample with phospholipase D which does not react with sphingomyelin and lysophosphatidylcholine but reacts with phosphatidylcholine, the lysophospholipase or the monoglyceride lipase, and the choline oxidase is performed at 10° to 50° C. for 1 to 60 minutes, and
the reaction of the resultant with a phospholipase D which does not react with glycerol-3-phosphorylcholine and free fatty acid but reacts with sphingomyelin, and the reduced choline oxidase is performed at 10° to 50° C. for 1 to 60 minutes.

16. The method according to claim 15, wherein the formed hydrogen peroxide is eliminated simultaneously with the reaction of the sample with phospholipase D which does not react with sphingomyelin and lysophosphatidylcholine but reacts with phosphatidylcholine, the lysophospholipase or the monoglyceride lipase, and the choline oxidase.

17. The method according to claim 2, wherein the reaction of the sample with phospholipase D which does not react with sphingomyelin and lysophosphatidylcholine but reacts with phosphatidylcholine, the lysophospholipase or the monoglyceride lipase, and the choline dehydrogenase is performed at 10° to 50° C. for 1 to 60 minutes, and
the reaction of the resultant with a phospholipase D which does not react with glycerol-3-phosphorylcholine and free fatty acid but reacts with sphingomyelin, and the reduced coenzyme oxidase is performed at 10° to 50° C. for 1 to 60 minutes.

18. The method according to claim 17, wherein the formed hydrogen peroxide is eliminated simultaneously with the reaction of the sample with phospholipase D which does not react with sphingomyelin and lysophosphatidylcholine but reacts with phosphatidylcholine, the lysophospholipase or the monoglyceride lipase, and the choline dehydrogenase.

19. The method according to claim 5, wherein the azide is lithium azide, sodium azide or potassium azide.

20. The method according to claim 10, wherein the azide is lithium azide, sodium azide or potassium azide.

21. The method according to claim 15, wherein the concentration of phospholipase D which does not react with sphingomyelin and lysophosphatidylcholine but reacts with phosphatidylcholine, the lysophospholipase or the monoglyceride lipase, and the choline oxidase is 0.001 to 200,000 U/L.

22. The method according to claim 17, wherein the concentration of phospholipase D which does not react with sphingomyelin and lysophosphatidylcholine but reacts with phosphatidylcholine, the lysophospholipase or the monoglyceride lipase, and the choline dehydrogenase is 0.001 to 200,000 U/L.

23. The method according to claim 21, wherein the concentration of phospholipase D which does not react with glycerol-3-phosphorylcholine and free fatty acid but reacts with sphingomyelin is 0.001 to 500,000 U/L.

24. The method according to claim 22, wherein the concentration of phospholipase D which does not react with glycerol-3-phosphorylcholine and free fatty acid but reacts with sphingomyelin is 0.001 to 500,000 U/L.

25. The method according to claim 24, wherein the concentration of oxidized coenzyme is 0.01 to 400 mmoles/L.

26. The method according to claim 25, wherein the concentration of reduced coenzyme oxidase in the reaction solution is 0.01 to 400,000 U/L.

27. The method according to claim 3, wherein the concentration of catalase is 0.001 to 1,000,000 U/L.

28. The method according to claim 10, wherein the concentration of catalase is 0.001 to 1,000,000 U/L.

29. The method according to claim 6, wherein the concentration of peroxidase in the reaction solution is 0.1 to 500,000 U/L.

30. The method according to claim 11, wherein the concentration of peroxidase in the reaction solution is 0.1 to 500,000 U/L.

\* \* \* \* \*